(12) United States Patent
Kwetkat et al.

(10) Patent No.: US 6,342,625 B1
(45) Date of Patent: Jan. 29, 2002

(54) AMPHIPHILIC COMPOUNDS WITH AT LEAST TWO HYDROPHILIC AND AT LEAST TWO HYDROPHOBIC GROUPS BASED ON AMIDES

(75) Inventors: Klaus Kwetkat, Lünen; Wulf Ruback, Dülmen, both of (DE)

(73) Assignee: RWE-DEA Aktiengesellschaft fuer Mineraloel und Chemie, Hamburg (DE)

( * ) Notice: Subject to any disclaimer, the term of this patent is extended or adjusted under 35 U.S.C. 154(b) by 0 days.

(21) Appl. No.: 08/817,930
(22) PCT Filed: Sep. 15, 1995
(86) PCT No.: PCT/EP95/03635
   § 371 Date: Jul. 2, 1997
   § 102(e) Date: Jul. 2, 1997
(87) PCT Pub. No.: WO96/14926
   PCT Pub. Date: May 23, 1996

(30) Foreign Application Priority Data

Nov. 11, 1994 (DE) .......................................... 44 40 328

(51) Int. Cl.$^7$ ........................ C07C 229/00; B01D 17/04
(52) U.S. Cl. ............. 560/169; 252/174.21; 252/174.22; 252/550; 510/119; 510/130; 510/276; 510/437; 558/166; 562/47; 564/153
(58) Field of Search ...................... 560/169; 252/174.21, 252/174.22, 550; 510/119, 130, 276, 437; 558/166; 562/47; 564/153

(56) References Cited

U.S. PATENT DOCUMENTS 5,160,450 A  11/1992  Okahara et al.
6,121,482 A  * 9/2000  Kwetkat et al. ............. 560/169

FOREIGN PATENT DOCUMENTS

| DE | 42 27 894 A1 | 2/1994 |
| EP | 0 258 923 | 3/1988 |
| JP | 60 096 695 A | 8/1985 |
| JP | 04124165 A | 9/1990 |
| WO | WO 95/11288 | 4/1995 |
| WO | WO/95/19955 | 7/1995 |

OTHER PUBLICATIONS

Micich et al, JAOCS, vol. 5, No. 5, pp 820–825, 1988.*
R. Zana & Y. Talmon, Letters to Nature, Mar. 18, 1993, vol. 362, pp. 228–230.
R. Zana, M. Benrraou, and R. Ruff, Alkanediyl–a,w–bis-(dismethylalkylammonium bromide) Surfactants. 1. Effect of the Spacer Chain Length on the Critical Micelle Concentration and Micelle Ionization Degree, Langmuir 1991/m 7, pp. 1072–1075.

* cited by examiner

Primary Examiner—Shailendra Kumar
(74) Attorney, Agent, or Firm—Oblon, Spivak, McClelland, Maier & Neustadt, P.C.

(57) ABSTRACT

The invention relates to amphiphilic compounds of general formula (I), ($R^1$, $R^3$—$C_1$-$C_{22}$ hydrocarbon radical, $R^2$—spacer, X, Y—functional groups, Z—1 to 10) with at least two hydrophilic and at least two hydrophobic groups on the basis of amides. The amphiphilic compounds of this invention are highly surface-active and are suitable in particular as emulsifiers, demulsifiers, detergents, dispersants and hydrotropics in industry and household, e.g. in the fields of metalworking, ore extraction, surface treatment, washing and cleaning, cosmetics, medicine and foodstuff processing and preparation.

20 Claims, No Drawings

AMPHIPHILIC COMPOUNDS WITH AT LEAST TWO HYDROPHILIC AND AT LEAST TWO HYDROPHOBIC GROUPS BASED ON AMIDES

This application is a 371 of PCT/EP95/03635, filed Sep. 15, 1995.

BACKGROUND OF THE INVENTION

1. Field of the Invention

The invention relates to amphiphilic compounds with at least two hydrophilic and at least two hydrophobic groups based on amides.

2. Description of the Background

A wide variety of anionic, cationic, nonionic and zwitterionic compounds are known as amphiphilic substances. By far the most of these substances consist of a hydrophilic head group and at least one hydrophobic part.

With the amphiphilic substances there is a need, for ecological reasons, for example concerning the reduction in the cost of packaging and transport, to achieve an increasingly greater effect per mass of substance employed. Since optimization by mixing amphiphilic substances produces only very limited advances, novel amphiphilic substances with greater efficiency are required. It is therefore necessary in particular to find substances with lower critical micelle concentrations and/or lower surface and interfacial tensions in order to be able to reduce markedly the amounts of active substance employed.

Initial approaches to a solution in this direction by doubling one part of the structure (hydrophilic head group, hydrophobic group) have already been disclosed. Thus, cationic surface-active compounds can be obtained by adding long-chain alkyl halides onto permethylated alkylenediamines [R. Zana, M. Benrraou, R. Rueff, Langmuir, 7 (1991) 1072: R. Zana, Y. Talmon, Nature, 362 (1993) 228; E. Alami, G. Beinert, P. Marie, R. Zana, Langmuir, 9 (1993) 1465].

Nonionic amides having a gemini structure are described in EP-A-O 258 923. They are employed in specific plasticizer and surfactant compositions and employed together with water-soluble quaternary ammonium compounds and a clay of a certain minimum ion-exchanger capacity.

Anionic surface-active compounds with at least two hydrophilic and at least two hydrophobic groups have to date been prepared only on the basis of diglycidyl ethers (U.S. Pat. No. 5,160,450, JP 01 304 033, JP 4 124 165). However, diglycidyl ethers are regarded as toxicologically objectionable and are rather costly. Furthermore, epichlorohydrin is used for their preparation, which leads to large amounts of residues so that these compounds are no longer in accord with the times from the ecotoxicological and economic viewpoints.

SUMMARY OF THE INVENTION

The object therefore was to find amphiphilic compounds which have at least two hydrophilic and at least two hydrophobic groups, the amphiphilic compounds having a very high efficiency relative to the amount used, and which furthermore can be prepared from raw materials which are easily available industrially and without large amounts of unwanted by-products being formed.

The object is achieved according to the invention by amphiphilic di- or oligoamides whose basic skeletons can be prepared from di- or oligoamines and fatty acids or fatty acid methyl esters. The corresponding di- or oligoamides can be alkoxylated. These nonionic amphiphilic compounds can be converted into anionic amphiphilic compounds by, for example, reacting the abovementioned compounds with $SO_3$/inert gas (or oleum or chlorosulfonic acid), with polyphosphoric acid, with a haloacetic acid, with a sultone or with a taurine and, in each case, subsequently neutralizing.

The amphiphilic compounds according to the invention are therefore compounds of the general formula I

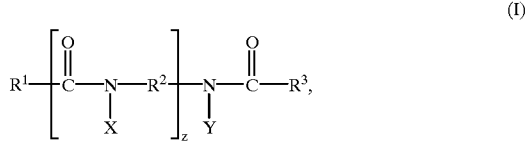

where $R^1$, $R^2$, $R^3$, X, Y and Z in formula I have the meanings described below:

$R^1$ and $R^3$ are, independently of one another, an unbranched or branched, saturated or unsaturated hydrocarbon radical with 1 to 22, preferably 7 to 17, carbon atoms.

Specific substituents $R^1$ and $R^3$ which may be mentioned are the radicals methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-uneicosyl, n-docosyl and their branched-chain isomers, and the corresponding singly, doubly or triply unsaturated radicals.

$R^2$ is a spacer consisting of an unbranched or branched chain with 2 to 100 carbon atoms, which in each case contains 0 to 20 oxygen and nitrogen atoms and 0 to 4 sulfur atoms and 0 to 3 phosphorus atoms, and which has 0 to 20 functional side groups such as, for example, hydroxyl, carbonyl, carboxyl, amino and/or acylamino groups.

The spacer $R^2$ is, in particular, as basic skeleton, unbranched or branched alkylene chains

with a=2 to 18, preferably a=3 to 6;

as basic skeleton, unbranched or branched alkenylene chains

with b+c=2 to 16, where b and c are each greater than zero;

as basic skeleton, unbranched or branched alkynylene chains

with d+e=2 to 16, where d and e are each greater than zero, and where in the basic skeletons according to formulae II to IV the spacer contains at any desired point in the chain additionally 0 to 4 carbonyl, amino or acylamino groups;

alicycles according to the formula V

with f and g=each 1 to 6 or according to formula VI

-3(4),8(9)-di(methylene)-tricyclo [$5.2.1.0^{2-6}$]decane-      (VI);

unsubstituted or substituted aromatics according to the formula VII $$—C_hH_{2h}—C_6R_4—(C_iH_{2i}—C_6R_4)_{j1}—C_{j2}H_{2j2}—$$ (VII)

or according to the formula VIII $$—C_hH_{2h}—C_{10}R_6—C_jH_{2j}—$$ (VIII)

with h, j, $j_1$ and $j_2$=each 0 to 8 and i=1 to 8 and with R=independently of one another in each case H or $C_1$- to $C_4$-alkyl;

a chain with functional side groups, in particular an amino, acylamino, carbonyl or carboxyl functionality.

Furthermore, the spacer $R^2$ in each case contains 0 to 20, preferably 1 to 12, oxygen and/or nitrogen atoms, 0 to 4 sulfur atoms and 0 to 3 phosphorus atoms, with at least one of the heteroatoms occurring at least once.

$R^2$ thus furthermore has in particular the meaning of a compound according to the formula IX $$—C_kH_{2k}—C_xR_y—Z—C_xR_y—C_lH_{2l}—$$ (IX)

with k and l=each 0 to 8, x=6 and y=4 or x=10 and y=6 or x=14 and y=8, and Z=O, NH, $NR^1$, N—C(O)$R^1$, $SO_2$, where $R^1$ is a hydrocarbon radical with 1 to 22 carbon atoms and R is, independently of one another, in each case H or $C_1$–$C_4$-alkyl;

of a compound according to the formula X $$—C_mH_{2m}—(OC_nH_{2n})_p—C_qH_{2q}—$$ (X)

with m=1 to 4, n=2 to 4, p=1 to 20, preferably p=1 to 4 and q=1 to 4, where mixed alkoxide units may also occur and then the sequence of the alkoxide units is arbitary;

of a compound according to the formula XI $$—C_rH_{2r}(RNC_sH_{2s})_t—C_uH_{2u}—$$ (XI)

or according to the formula XII $$—[C_rH_{2r}[RN—C(O)—NR]_t—C_uH_{2u}]_w—$$ (XII)

or according to the formula XIII $$—[C_rH_{2r}[RNC(O)C_xH_{2x}C(O)NR]_t—C_uH_{2u}]_w—$$ (XIII)

or according to the formula XIV $$—[C_rH_{2r}[RN—C(O)—CH=CH—C(O)—NR]_t—C_uH_{2u}]_w—$$ (XIV)

or according to the formula XV $$—[C_rH_{2r}[RNC(O)C_xR_yC(O)NR]_tC_uH_{2u}]_w—$$ (XV)

with r=2 to 4, s=2 to 4, t=1 to 20, preferably t=1 to 4, u=2 to 4, v=0 to 12, w=1 to 6, x=6 and y=4 or x=10 and y=6 or x=14 and y=8 with R=independently of one another in each case H or $C_1$- to $C_4$-alkyl.

X or Y is a substituent of the formula XVI $$—(C_2H_4O)_\alpha(C_3H_6O)_\beta H$$ (XVI)

with $\alpha$=0 to 50, preferably $\alpha$=10 to 30, $\beta$=0 to 60, preferably $\beta$=20 to 40, and $\alpha+\beta$=1 to 100, preferably $\alpha+\beta$=10 to 50, where $R^2$ is not $C_2H_4$ when $\beta$=0, and X or Y is a substituent of the formula XVII or X and Y are, independently of one another, substituents of the formula XVII $$—(C_2H_4O)_{6\varsigma}(C_3H_6O)_\delta—FR$$ (XVII)

with in each case
  $\gamma$=to 20, preferably $\gamma$=0 to 8,
  $\delta$=0 to 20, preferably $\delta$=0 to 12, and $\gamma+\delta$=1 to 40, preferably $\gamma+\delta$=5 to 20,
  where the alkoxide units are incorporated randomly or blockwise and the sequence is arbitrary and where FR is a functional radical —$CH_2$—COOM, —$SO_3$M, —P(O(OM))$_2$, —O—C(O)—$C_2H_3$($SO_3$M)—$CO_2$M' or —$C_2H_4$—$SO_3$M with M, M'=alkali metal, ammonium, alkanolammonium or ½ alkaline earth metal.

The degree of oligomerization Z is 1 to 10, preferably Z=1 to 4, particularly preferably Z=1.

The degree of alkoxylation is in each case an average and can assume any desired, including non-integral, value within the stated limits.

The amphiphilic compounds according to the invention are usually distinguished by extremely low critical micelle concentrations (CMC) and very low surface and interfacial tensions (for example in the presence of paraffin), which must be ascribed to their special structure—at least two hydrophilic groups and at least two hydrophobic groups. Furthermore, most of them display a rather high hydrophilic suspension capacity which is about halfway between that of conventional surfactants and that of pentasodium tripolyphosphate. Some of these compounds are extremely rapid wetting agents.

The amphiphilic compounds according to this invention are particularly suitable as emulsifiers, demulsifiers, detergents, dispersants and hydrotropes in industry and domestically, for example in the areas of metal processing, ore production, surface treatment, washing and cleaning, cosmetics, medicine and foodstuff processing and preparation.

In these cases they can be combined with all customary anionic, nonionic, cationic and ampholytic surface-active substances. Examples of nonionic surface-active substances which can be used for a combination and which may be mentioned are: fatty acid glycerides, fatty acid polyglycerides, fatty acid esters, ethoxylates of higher alcohols, polyoxyethylene fatty acid glycerides, polyoxyethylene/propylene glycol fatty acid esters, polyoxyethylene sorbitan fatty acid esters, polyoxyethylene castor oil or hardened castor oil derivatives, polyoxyethylene lanolin derivatives, polyoxyethylene fatty acid amides, polyoxyethylene alkylamines, alkanolamines, alkylamine oxides, derivatives of protein hydrolysates, hydroxy-mixed ethers, alkyl polyglycosides and alkylglucamides.

Examples of anionic surface-active substances which can be used for combinations and which may be mentioned are: soaps, ether carboxylic acids and salts thereof, alkylsulfonates, α-olefinsulfonates, sulfonates of higher fatty acid esters, higher alcohol sulfates, alcohol ether sulfates, hydroxy-mixed ether sulfates, salts of phosphate esters, taurides, isethionates, linear alkylbenzenesulfonates, cumenesulfonate, alkylarylsulfonates, sulfates of polyoxyethylene fatty acid amides and salts of acylamino acids.

Examples of customary cationic surface-active substances which can be used for combinations and which may be mentioned are: alkyltrimethylammonium salts, dialkyldimethylammonium salts, alkyldimethylbenzylammonium salts, alkylpyridinium salts, alkylisoquinolinium salts, benzethonium chlorides and cationic acylamino acid derivatives.

Examples of ampholytic surface-active substances which can be used for combinations and which may be mentioned are: amino acids, betaines, sulfobetaines, imidazoline derivatives, soybean oil lipids and lecithin.

Furthermore, the amphiphilic compounds according to the invention can also be combined together on their own. It is likewise possible to add conventional additives to the amphiphilic compounds according to the invention. Such additives are specifically selected for a formulation and normally comprise inorganic salts such as sodium chloride and sulfate, and builders, hydrotropes, UV absorbers, softening agents, chelating agents, viscosity modifiers and fragrances.

The abovementioned compounds can be prepared by known methods: the di- or oligoamines are reacted with, in each case, one equivalent of fatty acid or fatty acid methyl ester per free NH functionality at elevated temperatures (80 to 180° C.), optionally in the presence of a catalyst, removing the water which is produced or the methanol under vacuum. Subsequently, alkoxylation is carried out at temperatures from 130 to 190° C. in the presence of a basic catalyst. The products are liquids or soften at low temperatures and can subsequently be reacted with $SO_3$/inert gas (oleum or chlorosulfonic acid) or polyphosphoric acid or with a haloacetic acid, a sultone or with isethionic acid and neutralized with aqueous alkali metal or alkaline earth metal hydroxides or aqueous ammonia or alkanolamines. If required, the products are bleached in aqueous solution with hydrogen peroxide (0.1 to 2.0% based on solids).

EXAMPLES

The following examples are intended to illustrate the invention but not restrict it thereto. All percentage data are percentages by weight.

Example 1

$R^1=R^3 =$—$C_7H_{15}$/—$C_9H_{19}$ (1:1), $R^2=$—$C_2H_4$—, X, Y=—$(C_2H_4O)_5SO_3Na$ 91.8 g of ethylenediamine are mixed with 441.5 g of a mixture (1:1) of methyl octanoate and methyl decanoate in a 1 l four-neck flask with stirrer, thermometer, water trap and connected reflux condenser and heated to 120 to 140° C. Over the course of 7 hours, 72.3 ml of methanol are removed and the reaction is then stopped. The purity of the three diamides resulting from the mixture of homologs is checked by $^{13}$C NMR and is >99 mol %, yield 447.2 g (85% of theory).

170.0 g of the diamide mixture are mixed with 150 ml of white spirit, and 1.1 g of solid potassium hydroxide are added. The mixture is reacted at 160° C. with 220 g of ethylene oxide over the course of 6 hours. The catalyst is neutralized with lactic acid, and the precipitated potassium salt and any unreacted diamides are removed by filtration. The conversion of ethylene oxide is checked for completeness by weighing the product, and the ratio of ethylene oxide to the remainder of the molecule is determined by $^{13}$C NMR: 10 EO units per remainder of the molecule, yield: 390 g (quantitative), no remaining N—H functionalities in the product mixture according to IR.

218.5 g of the resulting ethoxylate in 300 ml of dichloromethane are added dropwise to a mixture of 117.7 g of chlorosulfonic acid and 60.2 g of acetic acid in such a way that the temperature does not exceed 5° C. The mixture is then stirred at room temperature for 3 hours (the ethoxylate is completely reacted according to check by thin-layer chromatography). It is neutralized with 2 normal sodium carbonate solution and diluted with saturated sodium bicarbonate solution. The product is extracted with n-butanol. and then the alcohol is removed. The purity is checked by thin-layer chromatography and NMR. Yield: 96.8 g (36% of theory), purity: 90%; characteristics with $^{13}$C NMR data (DMSO-$D_6$): 171.8 ppm, 69.2 ppm, 68.7 ppm, 67.8 ppm, 64.6 ppm, 62.3 ppm, 32.9 ppm, 30.7 ppm, 27.9–28.3 ppm, 24 ppm (broad), 21.9 ppm, 13.1 ppm; CMC: 0.011 g/l, $\gamma_{CMC}$=30 mN/m (in deionized water, 20° C.) $\gamma_{paraffin}$=2.5 mN/m (0.1 g/l active substance in deionized water, 20° C.).

Example 2

$R^1=R^3=$—$C_7H_{15}$/—$C_9H_{19}$ (1:1), $R^2=$—$C_2H_4$—, X, Y=—$(C_2H_4O)_{10}SO_3Na$

The reaction is carried out in analogy to Example 1: The same diamide mixture is prepared as in Example 1.

Ethoxylation: 170 g of diamide mixture, 150 ml of white spirit, 440 g of ethylene oxide, 1.1 g of KOH, according to NMR 20 EO units per remainder of the molecule, yield: 610 g (quantitative).

Sulfation: 217.5 g of ethoxylate, 78.8 g of chlorosulfonic acid, 40.3 g of acetic acid, yield: 123.7 g (50% of theory), purity: 90%, characteristic $^{13}$C NMR data ((DMSO-$D_6$): 172.0 ppm, 69.4 ppm, 69.1 ppm, 65.2 ppm, 28.5 ppm (broad), 21.1 ppm, 13.4 ppm, CMC: 0.13 g/l, $\gamma_{CMC}$=33 mN/m (in deionized water, 20° C.), $\gamma_{paraffin}$=15.5 mN/m (0.1 g/l active substance in deionized water, 20° C.).

Example 3

$R^1=R^3=$—$C_7H_{15}$/—$C_9H_{19}$ (1:1) $R^2=$—$C_6H_{12}$—, X, Y=—$(C_2H_4O)_8SO_3Na$

The reaction is carried out in analogy to Example 1: 116.2 g of hexamethylenediamine, 344.0 g of mixture (1:1) of octanoic and decanoic acids, 0.2 g of ZnO, reaction time: 7 hours, reaction temperature: 140 to 145° C., yield of diamide mixture: 465 g, purity: >95%;

ethoxylation: 170 g of diamide mixture, 150 ml of white spirit, 292 g of ethylene oxide, 1.1 g of KOH, yield of ethoxylate: 370 g, 8 EO units per remainder of the molecule;

Sulfation: in analogy to Example 1 Yield: 105.4 g (62% of theory), purity: 92%, characteristics $^{13}$C NMR data (DMSO-$D_6$): 173.4 ppm (broad), 70.4 ppm, 69.3 ppm, 68.9 ppm, 68.1 ppm, 33.1 ppm, 28 to 29 ppm (broad), 22.0 ppm, 13.0 ppm; CMC: 0.016 g/l, $\gamma_{CMC}$=28.5 mN/m (in deionized water, 20° C.), $\gamma_{paraffin}$=3.0 mN/m (0.1 g/l active substance in deionized water, 20° C.).

What is claimed is:

1. Anionic amphiphilic compounds of the general formula I

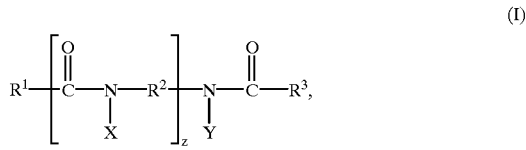

(I)

in which $R^1$ and $R^3$ are, unbranched or branched, saturated or unsaturated independently of one another, a hydrocarbon radical with 1 to 22 carbon atoms, $R^2$ is a spacer, and X and Y are, independently of one another, alkoxylated substituents, whereby at least one of X or Y is a substituent of the formula XVII

with γ=0 to 20, δ=0 to 20, and γ+δ=1 to 40, and FR is a functional radical —$CH_2$—COOM, —$SO_3$M, —P(O)$(OM)_2$, —C(O)—$C_2H_3(SO_3M)$—$CO_2$M', or $C_2H_4$—$SO_3$M with M, M'=alkali metal, ammonium, alkanolammonium or ½ alkaline earth metal whereby the alkoxide units are incorporated randomly or blockwise and the sequence is arbitrary, and the degree of oligomerization Z=1 to 10.

2. Amphiphilic compounds according to claim 1, wherein the hydrocarbon radicals $R^1$ and $R^3$ are unbranched or branched, saturated or unsaturated, the spacer $R^2$ is an unbranched or branched chain with 2 to 100 carbon atoms, which in each case contains 0 to 20 oxygen and nitrogen atoms and 0 to 4 sulphur atoms and 0 to 3 phosphorus atoms, and which has 0 to 20 functional side groups.

3. Amphiphilic compounds according to claim 1, wherein the degree of oligomerization Z=1 to 4.

4. Amphiphilic compounds according to claim 1, wherein the hydrocarbon radicals $R^1$ and $R^3$ in the formula (I) contain, independently of one another, 7 to 17 carbon atoms.

5. Amphiphilic compounds according to claim 1, wherein $R^2$ is a spacer which consists of an unbranched or branched alkylene chain of the formula II

with a=2 to 18, or of an unbranched or branched alkenylene chain of the formula III

with b+c=2 to 16, where b and c are each greater than zero, or of an unbranched or branched alkynylene chain of the formula IV

with d+e=2 to 16, where d and e are each greater than zero, and where in the skeletons of the spacer according to formulae II to IV the spacer contains at any desired point in the chain 0 to 4 carbonyl, amino or acylamino groups.

6. Amphiphilic compounds according to claim 1, wherein $R^2$ is a spacer which consists of alicycles according to the formula V

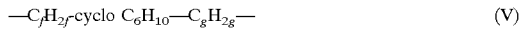

with f and g=each 1 to 6 or according to the formula VI

-3(4),8(9)-di(methylene)-tricyclo[5.2.1.0$^{2,6}$]decane- (VI).

7. Amphiphilic compounds according to claim 1, wherein $R^2$ is a spacer which consists of unsubstituted or substituted aromatics according to the formula VII

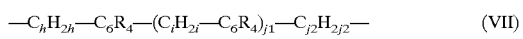

or according to the formula VIII

with h, j, j1 and j2=each 0 to 8 and i=1 to 8 and with R=independently of one another in each case H or C1- to C4-alkyl.

8. Amphiphilic compounds according to claim 1, wherein the spacer $R^2$ carries functional side groups, in particular amino, acylamino, carbonyl or carboxyl functionalities.

9. Amphiphilic compounds according to claim 1, wherein the spacer $R^2$ in each case contains 0 to 20 oxygen and/or nitrogen atoms, 0 to 4 sulphur atoms and 0 to 10 phosphorus atoms, and at least one of the heteroatoms occurs at least once.

10. Amphiphilic compounds according to claim 9 wherein $R^2$ is a spacer according to the formula (IX)

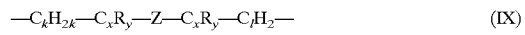

with k and l =each 0 to 8, x=6 and y=4 or x=10 and y=6 or x=14 and y=8, and Z=O, CO, NH, $NR^1$, —N—C (O)$R^1$, —$SO_2$ where $R^1$ is a hydrocarbon radical with 1 to 22 carbon atoms and R is, independently of one another, in each case H or C1–C4-alkyl.

11. Amphiphilic compounds according to claim 9, wherein $R^2$ is a spacer according to the formula X,

with m=1 to 4, n=2 to 4, p=1 to 20, and q=1 to 4, where mixed alkoxide units may also occur and then the sequence of the alkoxide units is arbitrary.

12. Amphiphilic compounds according to claim 9, wherein $R^2$ is a spacer according to the formula XI,

or according to the formula XII

or according to formula XIII

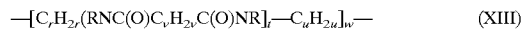

or according to formula XIV

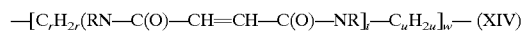

or according to formula XV

with r=2 to 4, s=2 to 4, t=1 to 20, u=2 to 4, v=0 to 12, w=1 to 6, x=6 and y=4 or x=10 and y=6 or 10, x=14 and y=8 with R=independently of one another in each case H or C1- to C4-alkyl.

13. A process, comprising using the amphiphilic compounds according to claim 1 as emulsifiers or demulsifiers.

14. A process comprising using the amphiphilic compounds according to claim 1 as auxiliaries in metal processing, ore production or surface treatment.

15. A process for using amphiphilic compounds as a textile auxiliary or for cleaning and washing textiles, comprising contacting a textile with the amphiphilic compounds according to claim 1.

16. A method of cleaning a hard surface, comprising contacting a hard surface with the amphiphilic compounds according to claim 1.

17. A method for cleaning and washing skin or hair, comprising contacting skin or hair with the amphiphilic compounds according to claim 1.

18. Amphiphilic compounds according to claim 1, wherein the alkoxylated substituents X and Y not containing a functional radical are, independently of one another, substituents of the formula XVI $$—(C_2H_4O)_\alpha(C_3H_6O)_\beta H \qquad (XVI)$$

with $\alpha=0$ to 50, $\beta=0$ to 60, and $\alpha+\beta=1$ to 100, where the alkoxide units are incorporated randomly or blockwise and the sequence is arbitrary.

19. Amphiphilic compounds according to claim 1, wherein X and Y are, independently of one another, substituents of the formula XVII $$—(C_2H_4O)_\gamma(C_3H_6O)_{67}—FR \qquad (XVII)$$

with in each case $\gamma=0$ to 8, $\delta=0$ to 12, and, $\gamma+\delta=5$ to 20.

20. Amphiphilic compounds according to claim 1, wherein alkoxylated substituents X and Y not containing a functional radical are, independently of one another, substituents of the formula XVIII $$—CH_2[CHO(C_2H_4O)_{68}(C_3H_6O)_\eta H]_z—CH_2— \\ O(C_2H_4O)_\mu(C_3H_6O)_\sigma—H \qquad (XVIII)$$

with $z=3$ to 6, and $\epsilon$ or $\mu=0$ to 30, and $\eta$ or $\sigma=0$ to 30 and where the alkoxide units are likewise incorporated randomly or blockwise and the sequence is arbitray.

* * * * *

UNITED STATES PATENT AND TRADEMARK OFFICE
CERTIFICATE OF CORRECTION

PATENT NO. : 6,342,625 B1
DATED : January 29, 2002
INVENTOR(S) : Klaus Kwetkat et al.

It is certified that error appears in the above-identified patent and that said Letters Patent is hereby corrected as shown below:

Column 8,
Line 9, "$-C_kH_{2k}-C_xR_y-Z-C_xR_y-C_lH_2-$" should read -- $-C_kH_{2k}-C_xR_y-Z-C_xR_y-C_lH_{2l}-$ --.

Column 9,
Line 10, "$-(C_2H_4O)_\gamma(C_3H_6O)_{67}-FR$" should read -- $-(C_2H_4O)_\gamma(C_3H_6O)_\delta-FR$ --.

Column 10,
Line 5, "$CH_2[CHO(C_2H_4O)_{68}(C_3H_6O)_\eta H]_z-CH_2-O(C_2H_4O)_\mu(C_3H_6O)_\sigma-H$" should read -- $CH_2[CHO(C_2H_4O)_\varepsilon(C_3H_6O)_\eta H]_z-CH_2-O(C_2H_4O)_\mu(C_3H_6O)_\sigma-H$ --.

Signed and Sealed this

Twenty-second Day of October, 2002

Attest:

JAMES E. ROGAN
Attesting Officer   Director of the United States Patent and Trademark Office